United States Patent [19]

Antowski

[11] Patent Number: 4,754,748

[45] Date of Patent: Jul. 5, 1988

[54] APPARATUS FOR GENERATING PNEUMATIC PRESSURE PULSES FOR APPLICATION TO THE EXTERNAL ACOUSTIC MEATUS OF A PATIENT

[76] Inventor: Jerry Antowski, SÅngvägen 54, S-175 36 Järfälla, Sweden

[21] Appl. No.: 857,753
[22] PCT Filed: Aug. 30, 1985
[86] PCT No.: PCT/SE85/00323
 § 371 Date: Apr. 16, 1986
 § 102(e) Date: Apr. 16, 1986
[87] PCT Pub. No.: WO86/01399
 PCT Pub. Date: Mar. 13, 1986

[30] Foreign Application Priority Data

Aug. 31, 1984 [SE] Sweden ................................ 8404375

[51] Int. Cl.⁴ ........................ A61H 23/00; A61B 5/12; A61B 5/03
[52] U.S. Cl. ........................ 128/40; 128/38; 128/746; 128/64
[58] Field of Search ............. 128/38, 40, 746, 747, 128/39, 64, 32, 54, 44, 24 R

[56] References Cited

U.S. PATENT DOCUMENTS

| 841,146 | 1/1907 | Hasbrouck | 128/40 |
|---|---|---|---|
| 976,200 | 11/1910 | Meyer | 128/39 |
| 1,678,564 | 7/1928 | Eldred | 128/38 |
| 1,678,565 | 7/1928 | Eldred | 128/38 |
| 2,014,009 | 9/1935 | Vance | 128/40 |
| 2,264,422 | 12/1941 | Wells | 128/38 |
| 2,626,601 | 1/1953 | Riley | 128/38 |
| 2,652,048 | 9/1953 | Joers | 128/39 |
| 4,325,386 | 4/1982 | Katz | 128/746 X |
| 4,459,996 | 7/1984 | Teele | 128/746 |
| 4,462,411 | 7/1984 | Rickards | 128/746 |
| 4,556,069 | 12/1985 | Dalton, Jr. et al. | 128/746 |

FOREIGN PATENT DOCUMENTS

| WO83/02556 | 8/1983 | PCT Int'l Appl. | |
| 812287 | 3/1981 | U.S.S.R. | 128/38 |

Primary Examiner—Edgar S. Burr
Assistant Examiner—Tonya Lamb
Attorney, Agent, or Firm—Browdy and Neimark

[57] ABSTRACT

An apparatus for producing pressure pulses intended for application to the external acoustic meatus of a patient, for the purpose of influencing the hydrodynamic system of the inner ear in the treatment of certain diseases, particularly Menieres disease, comprises two rotary air-pumps (1, 2) of variable, controllable speed. Respective pressure sides of the two pumps (1, 2) can be selectively connected to and disconnected from a common pressure-pulse output line (7), by means of a respective controllable valve (5, 6). The pumps are driven by electric motors (3, 4) and the rotational speed of the motors and the settings of the electrically operable valves (5, 6) are controlled by a control unit (9) incorporating a microprocessor, in response to a program relating to a desired shape, frequency, amplitude, duration etc. of the generated pressure pulses, this program being stored in the control unit. The apparatus also includes a pressure transducer (8) which is connected to the output line (7) and which produces a signal representing the momentary pressure prevailing in the output line (7), this signal being applied to the control unit and used therein to control the two pumps (1, 2) and the two valves (5, 6).

10 Claims, 2 Drawing Sheets

APPARATUS FOR GENERATING PNEUMATIC PRESSURE PULSES FOR APPLICATION TO THE EXTERNAL ACOUSTIC MEATUS OF A PATIENT

The present invention relates to an apparatus for generating pneumatic pressure pulses for application to the external acoustic meatus, the ear opening, of a patient in order to influence the hydrodynamic system of the inner ear.

It has been possible to establish that changes in the hydrodynamic system of the inner ear, including the endolymph and perilymph, affect the function of the ear and can be thought to be the cause of various disease conditions. One such disease is Ménières disease, the symptoms of which are extremely troublesome to the patient, such as disturbed balance, vertigo, impaired hearing, singing noises in the ear, tinnitus, etc.. Medical tests have shown that these symptoms can be eased considerably, and in many cases completely cured, by means of a course of treatment in which pneumatic pressure pulses are applied to the external acoustic meatus of the patient, these pressure pulses propagating through the middle ear to the inner ear and there influencing the hydrodynamic system of the said inner ear. Propagation of the pressure pulses from the external acoustic meatus to the inner ear can be facilitated by implanting in the patient a transmyringial tube, made for example of Teflon ®. Those tests which have been carried out with this form of treatment have shown that in order to obtain the best results, it must be possible to vary and to determine precisely, inter alia, the shape, frequency and amplitude of these pulses in respect of each individual patient.

For the purpose of generating the pressure pulses necessary in this form of treatment there has earlier been proposed, and used, apparatus which include one or more membrane pumps, pressure reservoirs, mechanically adjustable throttle devices, etc., such as described in the International Patent Application No. PCT/SE83/00013, Publication Number WO 83/02556. Great difficulties have been experienced, however, in producing with sufficient accuracy pressure pulses which have the particular parameters necessary for each individual patient, e.g. such parameters as pulse shape, frequency and amplitude, by means of these earlier proposed and used apparatus. A prime difficulty in this respect is one of avoiding the temporary occurrence of underpressure in the external acoustic meatus, such underpressures being undesirable.

Accordingly, the object of the present invention is to provide a novel and improved apparatus for generating the pneumatic pressure pulses desired in the form of treatment aforedescribed in which those pressure-pulse parameters of interest can be readily varied and determined with a high degree of accuracy, stability and reliability.

The characterizing features of the apparatus according to the invention are set-forth in the following claims.

The invention will now be described in more detail with reference to the accompanying drawing, in which FIG. 1 is a diagram illustrating a typical shape of the pressure pulses to be produced by the apparatus according to the invention;

Figure 1:
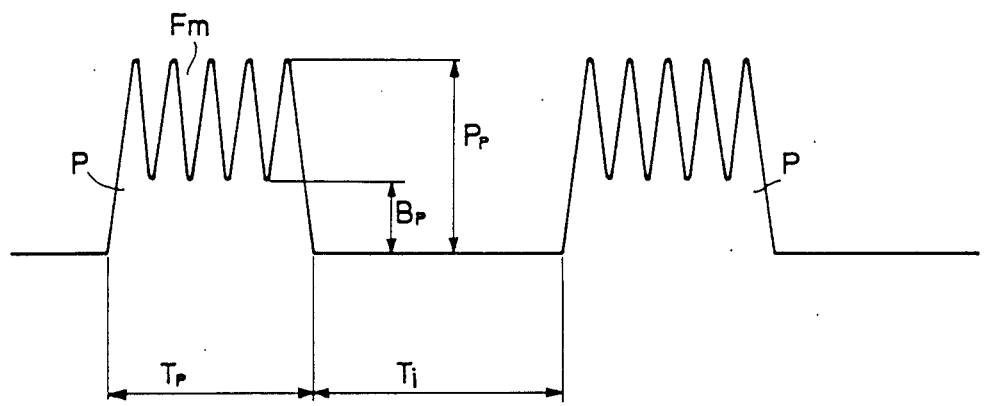

The diagram in FIG. 1 exemplifies a typical shape of the pressure pulses to be produced by the apparatus according to the invention. The treatment cycle consists of a plurality of mutually sequential pressure pulses P, having a substantially sinusoidal modulation. Those parameters of interest when effecting treatment are:

the pulse base pressure $B_p$,
the maximum pulse pressure $P_p$,
the pulse modulation frequency $F_m$,
the individual pulse length $T_p$, and
the pulse time-spacing $T_i$ The total number of pulses P in each pulse series is also of interest, as is optionally also the number of such pulse series when a plurality of pulse series is applied to the patient during the course of a single treatment period, and therewith the time lapse from the end of one pulse series to the beginning of the next.

In order to achieve the best possible results from the treatment administered, it shall be possible to vary all of these pressure-pulse parameters in a ready and simple manner, and to set the parameters to desired values with a high degree of accuracy and reliability in dependence on the needs of each individual patient. It shall be noted in this respect that the parameters $B_p$, $P_p$, $T_p$, $T_i$ and $F_m$ need not necessarily be the same for all pulses in a pulse series. In addition, it is preferred that no underpressure occurs, for example at the end of each pulse. Examples of suitable setting ranges for individual parameters are:

$B_p = 0\text{--}30$ mb
$P_p = 0\text{--}30$ mb
$T_p = 0.1\text{--}60$ s
$T_i = 0\text{--}60$ s
$F_m = 0\text{--}20$ Hz The total length of a pulse series can be set for times of up to 10 minutes. The time spacing between mutually sequential pulse series, when applying a number of such series, can also be set to values of up to 10 minutes.

Figure 2:
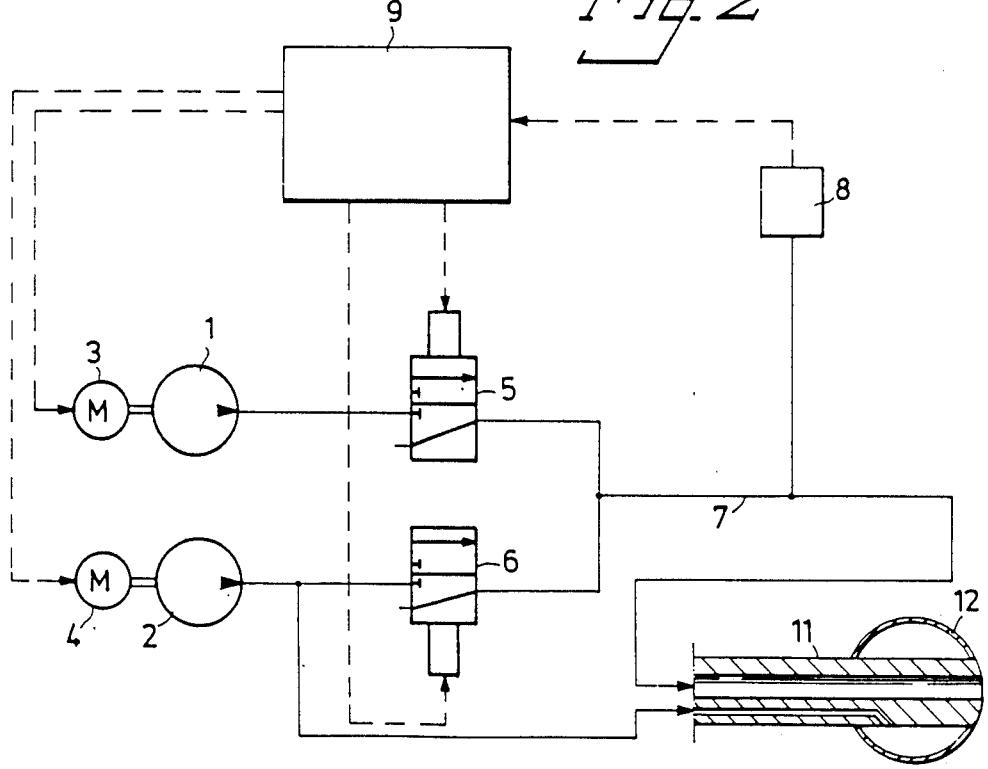
FIG. 2 is a simplified pneumatic-electric block diagram of one embodiment of apparatus according to the invention.

As illustrated by way of example in FIG. 2, the pressure-pulse generating apparatus according to the invention comprises two rotary air pumps 1 and 2 which are driven continuously at variable, controllable speeds by means of a respective electric motor 3 and 4. The pumps 1,2 may be sliding-vane type pumps, and the pumps with associated drive motors may, for example, be of the kind retailed under the name Microvac 3 by the Company Edwards, England. Each of the pressure sides of the two pumps is connected to a respective electrically controllable, 3-way, 2-position micro-valve 5 and 6. The micro-valves may, for example, be of the type LFAA 1200118H from the Lee Company, Connecticut, USA. Each of the pumps 1,2 can be connected to a common output hose or line 7 by means of the microvalves 5,6, or so that this connection can be broken. When one of the valves 5,6 breaks the connection between the associated pump 1 or 2 and the output hose, this valve simultaneously places the hose 7 in communication with ambient atmosphere. The output hose 7, in which the pressure pulses generated by the apparatus occur, is connected at its distal end to a suitably designed ear plug 11, which can be inserted into the external acoustic meatus of a patient, so as to connect the hose 7 thereto in a pressure-tight manner. The ear plug 11 may advantageously be provided with an inflatable cuff 12, for sealing engagement with the walls of the external acoustic meatus. The pressure required to seal the cuff 12 against said walls may suitably be taken from the pressure side of pump 2. The apparatus also includes a pressure transducer 8, which is connected to the output hose or like line 7 and which produces an electric signal representing the momentary pressure in the hose 7. The pressure transducer 8 may, for example, comprise a micro-pressure-transducer of the type KPY32R from Siemens AG.

The apparatus also incorporates a control unit 9, which is arranged to receive the pressure signal produced by the transducer 8 and which controls the pump drive motors 3,4 and the settings of respective valves 5 and 6. The control unit 9 includes a microprocessor which is suitably constructed for the aforesaid purpose and which operates in response to a program inserted and stored therein, this program containing all relevant data regarding the aforesaid parameters for the series of pressure pulses encompassed by the treatment intended for administration to a particular patient.

The pulse base pressure $B_p$ is determined by means of one of the aforesaid pumps, for example the pump 1, steering of the valve 5 connected to this pump determining the pulse length $T_p$ and the time spacing $T_i$ between mutually sequential pulses. The rotational speed of the second pump 2 will therewith determine the maximum pulse pressure $P_p$, whereas steering of the valve 6 connected to the other pump 2 will determine the modulation frequency $F_m$. It has been found that when using an apparatus of this construction the desired series of pressure pulses having parameters which are suitable for each individual patient can be produced to an extremely high degre of precision and stability. Because the valves 5,6 place the hose 7 in communication with ambient atmosphere when breaking the connections of the associated pumps 1,2 to the output hose 7, it is ensured, in a highly effective manner, that no deleterious pressure build-up will occur in the external acoustic meatus of the patient. The apparatus according to the invention also affords approximative sinusoidal modulation of the pressure pulses in a desirable manner, and totally avoids the occurrence of temporary underpressure in the hose 7.

An apparatus according to the invention can readily be given small dimensions, of the same order of magnitude as a conventional personal calling device, thereby enabling the patient to carry the device on his/her person and to administer treatment to himself/herself when found necessary.

Figure 3:
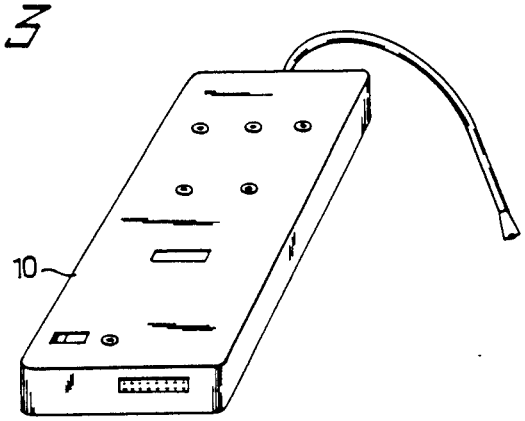
FIG. 3 illustrates an exemplifying embodiment of a proposed, conceivable external configuration of an apparatus according to the invention.
Figure 4:
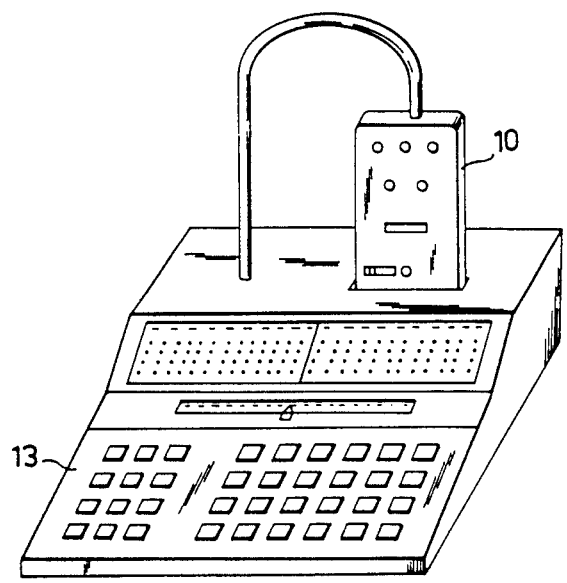
FIG. 4 illustrates an exemplifying embodiment of an apparatus according to the invention temporarily connected to a separate programming unit.

An apparatus according to the invention may also be provided with necessary auxiliary devices, for example a set of keys for entering a pulse-generation control program into the apparatus, or changing an existing program. The apparatus may also be provided with means for visual display and/or write-out of the pulse-generation control program stored in the control unit. An apparatus provided with such programming and display means is best suited for use in hospitals, medical treatment clinics, and by doctors. A compact, readily carried apparatus intended for the patient's personal use, is, on the other hand, suitably constructed so that when necessary it can be connected to a separate programming unit which is provided with a keyboard for entering a program into and changing an existing program in the apparatus when temporarily connected to the program unit, and which also incorporates display and/or write-out means for visual presentation of the program data stored in the temporarily connected apparatus. FIG. 3 illustrates by way of example a conceivable external design of such a patient apparatus 10, whereas FIG. 4 illustrates an exemplifying embodiment of one such personal apparatus 10 connected temporarily to a separate programming unit 13.

Such personal apparatus may also conceivably be constructed to enable it to be connected to any type of data terminal of standard design with respect to the aforesaid programming procedure. Such connection may also conceivably be effected with the aid of suitable modem through the telephone network.

An apparatus according to the invention which is intended to be used solely by one specific patient may also be constructed, to advantage, so that in addition to containing requisite data concerning the treatment program currently applicable to the patient, the apparatus control unit also contains a complete record of all previous treatment programs used in respect of the same patient, so that these previous programs can be visually presented or written-out for study by the dootor concerned, through the agency of a programming unit 13. The memory incorporated in the apparatus may also conveniently contain other pertinent data concerning the patient, so that the patient's doctor has ready access to such data.

It will be understood that an apparatus according to the invention may be constructed differently to the apparatus aforedescribed. For example, the pumps, valves and pressure transducers used may be different to those used in the described embodiment. In order to reduce the dimensions of the apparatus, two pumps combined to form an integral pump unit may be used for example.

I claim:

1. An apparatus for generating pneumatic pressure pulses for application to the external acoustic meatus of a patient for the purpose of influencing the hydrodynamic system of the inner ear, comprising:

two rotary air-pumps (1,2) of variable controllable speed;

two controllable valves (5,6) downstream of said two rotary air-pumps, one said valve receiving the output of one of said rotary air-pumps and another of said valves receiving the output of another of said air-pumps;

an output line (7) from said valves and a meatus mating means (11) for pressure-tight connecting with the external acoustic meatus of the ear of the patient along said output line; and control means (9) for controlling the speed of the two air-pumps (1,2) and the settings of the two valves (5,6) to produce a pulsed output of air to the output line (7), the meatus mating means (11) and the external acoustic meatus of the ear of the patient according to a preselected program controlling the shape, frequency and amplitude of the pressure pulses produced in the output line (7).

2. An apparatus according to claim 1 further comprising pneumatic means (12) to control said pressure-tight connection.

3. An apparatus according to claim 1, characterized in that the control unit is provided with, or is connectable to means for reading said program into the control unit.

4. An apparatus according to claim 1, characterized in that the control unit (9) is provided with, or is connectable to means for the visual presentation and/or write-out of data relating to the program stored in the control unit.

5. An apparatus according to claim 1, characterized in that said valves (5,6) are arranged to place the output line (7) in communication with the ambient atmosphere when breaking said connection between said output line (7) and the pressure side of the associated pump means (1,2).

6. An apparatus according to claim 5 characterized in that the control unit is provided with, or is connectable to means for reading said program into the control unit.

7. An apparatus according to claim 1, characterized by a pressure transducer (8) which is connected to said output line (7) and which is adapted to produce a signal representing the momentary pressure prevailing in the output line, this signal being applied to the control unit (9).

8. An apparatus according to claim 7 characterized in that the control unit is provided with, or is connectable to means for reading said program into the control unit.

9. An apparatus according to claim 7 characterized in that said valves (5,6) are arranged to place the output line (7) in communication with the ambient atmosphere when breaking said connection between said output line (7) and the pressure side of the associated pump means (1,2).

10. An apparatus according to claim 9 characterized in that the control unit is provided with, or is connectable to means for reading said program into the control unit.

* * * * *